United States Patent [19]

Anderton

[11] Patent Number: 4,797,907
[45] Date of Patent: Jan. 10, 1989

[54] BATTERY ENHANCED POWER GENERATION FOR MOBILE X-RAY MACHINE

[75] Inventor: Richard L. Anderton, West Jordan, Utah

[73] Assignee: Diasonics Inc., San Francisco, Calif.

[21] Appl. No.: 83,625

[22] Filed: Aug. 7, 1987

[51] Int. Cl.$^4$ ............................................. H05G 1/10
[52] U.S. Cl. .................... 378/101; 378/102; 378/103
[58] Field of Search ................. 378/101, 102, 103

[56] References Cited

U.S. PATENT DOCUMENTS 4,053,778  10/1977  Franke ................................ 398/102

Primary Examiner—Eugene R. LaRoche
Assistant Examiner—David Mis
Attorney, Agent, or Firm—Blakely, Sokoloff, Taylor & Zafman

[57] ABSTRACT

A mobile X-ray machine utilizes batteries to provide electrical power to produce high-voltage necessary to generate X-rays during a X-ray exposure. A battery charger circuit is used to supplement the battery during the X-ray exposure and charges the batteries during non-exposure periods. By using batteries to power the X-ray generating device, the X-ray machine is capable of being operated from 110 volt AC power sources permitting the machine to be mobile due to its ability of being operated from ordinary house current.

4 Claims, 6 Drawing Sheets

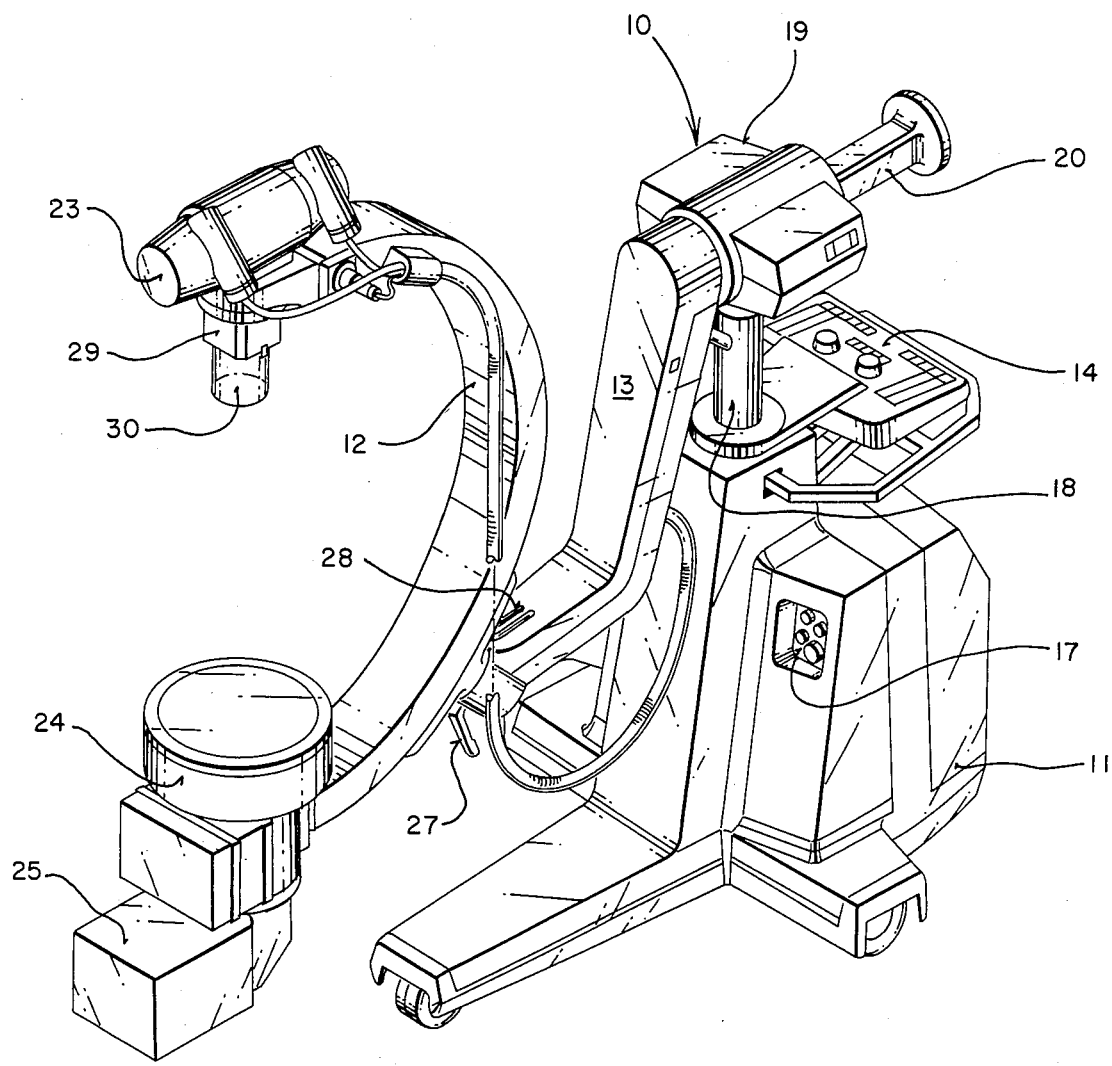
FIG_1

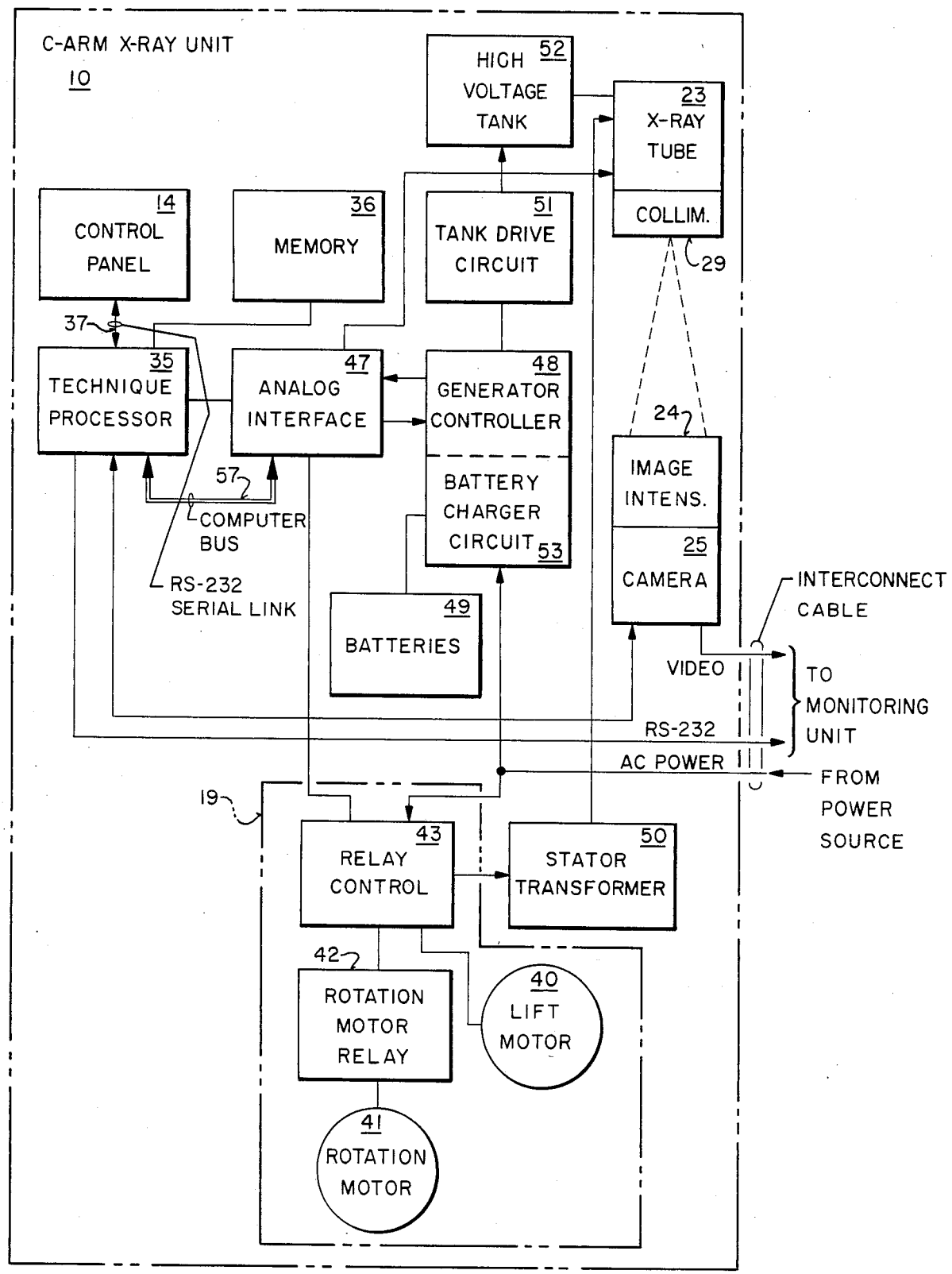

FIG_3A
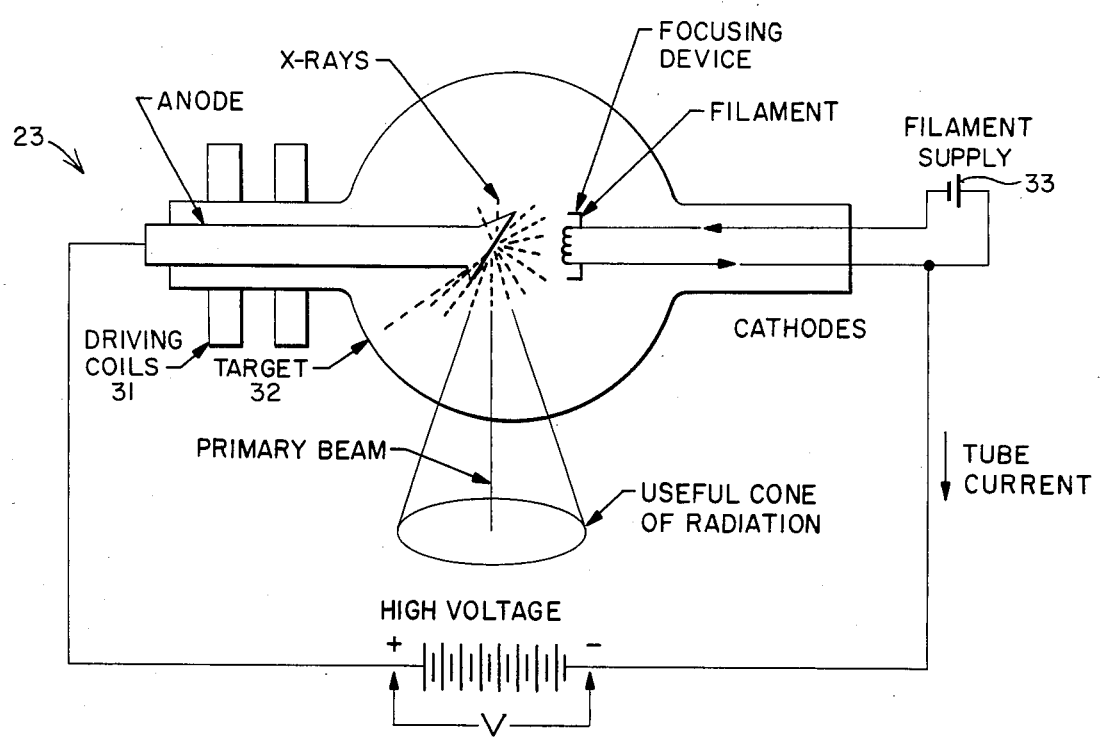
FIG_3B
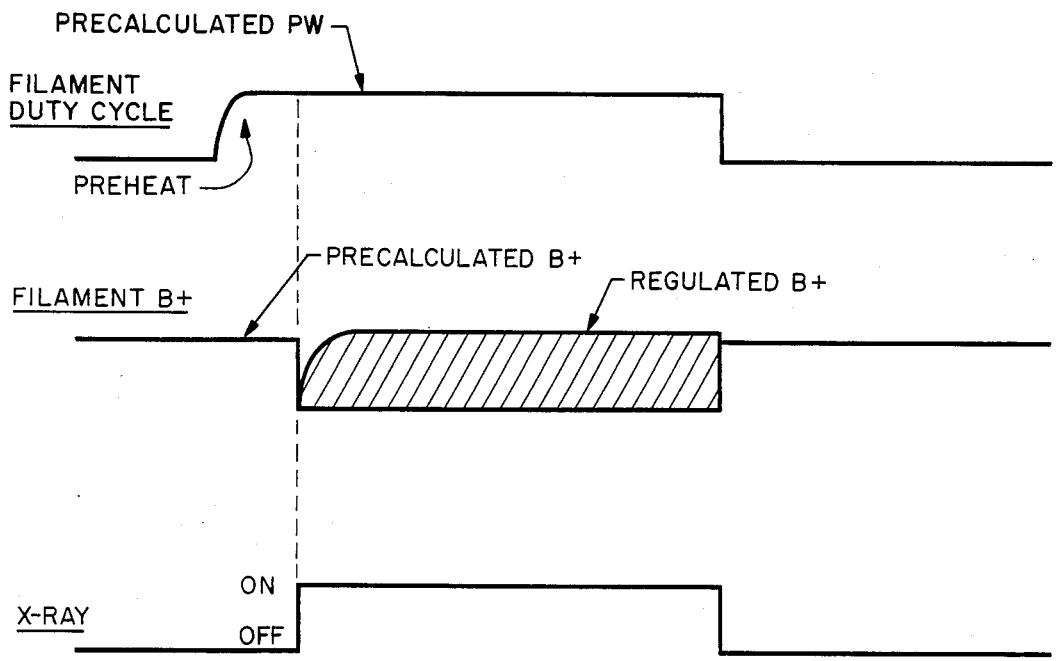

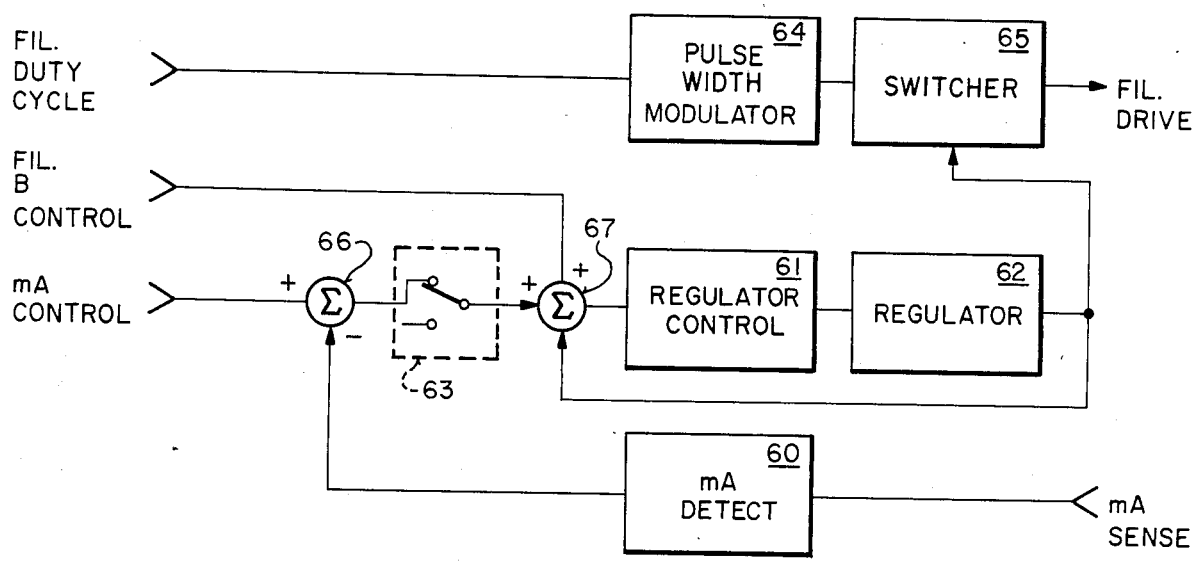
FIG_4
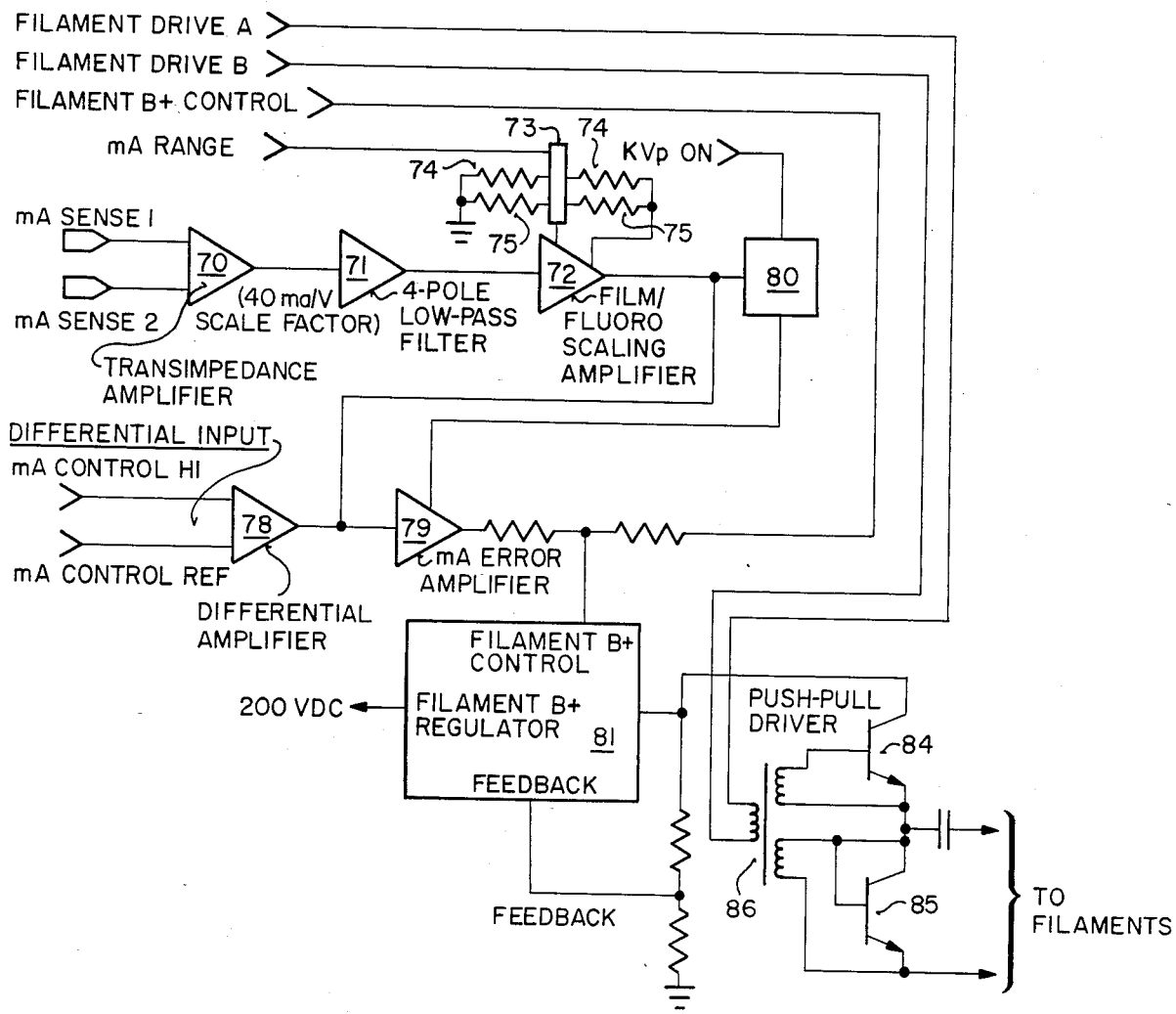
FIG_5

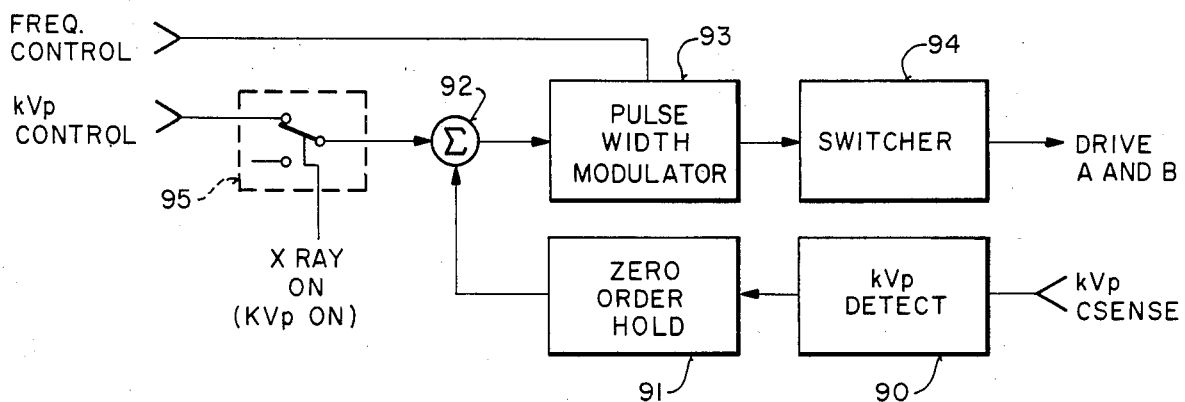
FIG_6
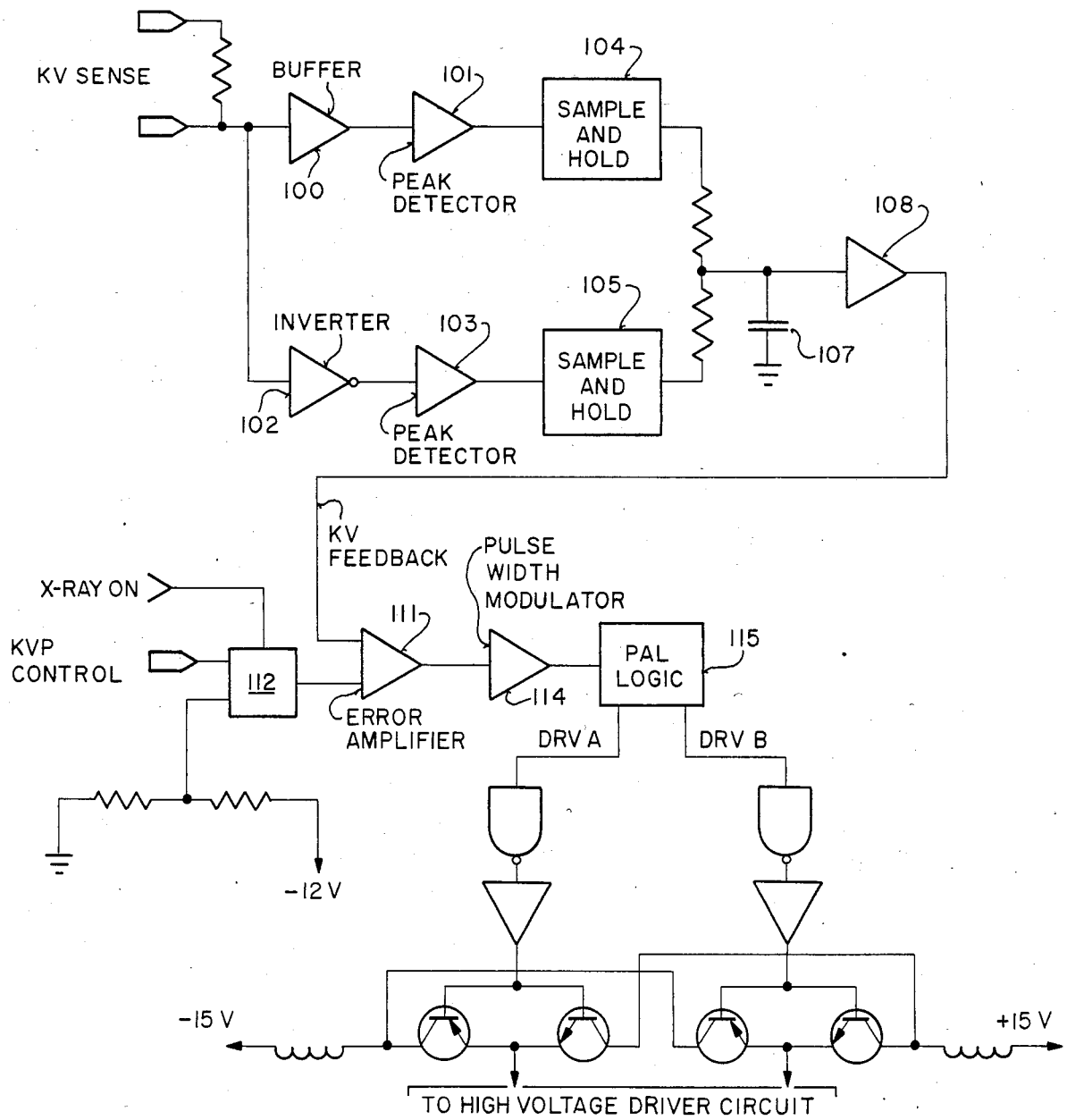
FIG_7

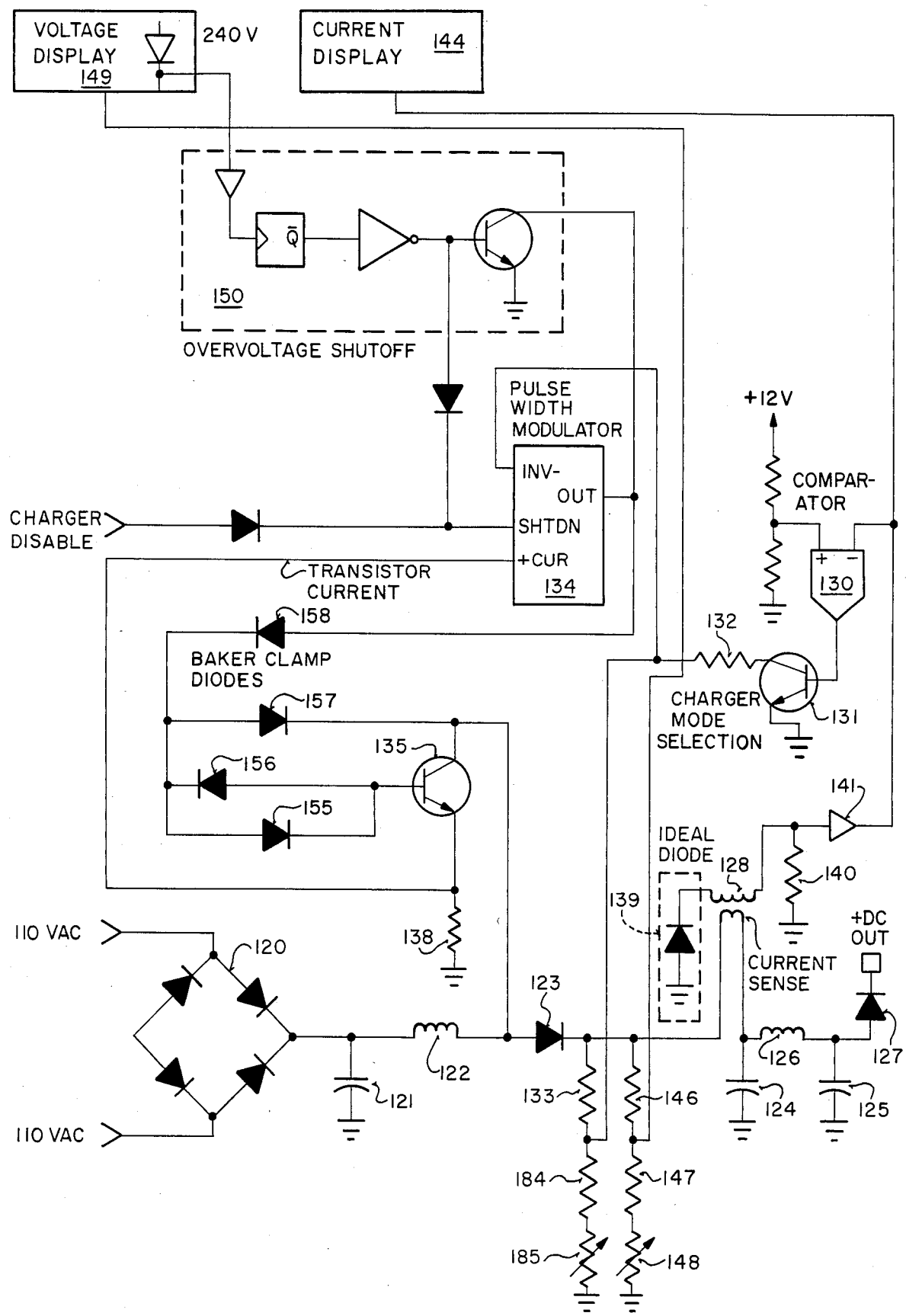
FIG_8

12# BATTERY ENHANCED POWER GENERATION FOR MOBILE X-RAY MACHINE

BACKGROUND OF THE INVENTION

1. Field of the Invention.

The present invention relates to the field of X-ray equipment and more specifically to mobile C-arm X-ray imaging systems.

2. Related Application.

The present application is related to a copending U.S. application Serial No. 083,626, filed Aug. 7, 1987, entitled "Dynamic Calibration for an X-Ray Machine", and assigned to the assignee of the present application.

3. Prior Art.

The use of X-ray equipment for medical diagnostics is well known in the prior art. The earlier X-ray devices were fixed devices requiring the patient to be brought to the unit for medical diagnosis. The earlier techniques involved a simple concept of shooting an X-ray beam through the patient and having the beam impinge on a photographic film, which resulted in a exposure of the film termed a "negative". As technology advanced, more sophisticated X-ray equipment became available. Instead of just providing a single exposure onto a photographic film, imaging systems were developed which permitted the diagnostician to view an image on a video monitoring screen. Further, with the advent of computer systems, it became possible to store image information for future use. In some instances, the operation of the X-ray equipment was under a control of a computer system.

However, the basic concept of taking an X-ray exposure has not changed since the earliest devices. That is, an X-ray emitter, such as an X-ray tube, transmits an X-ray beam and a receptor is disposed to receive this X-ray beam. When a patient (or an object to be viewed) is to be imaged, the patient is placed in the path of the beam between the emitter and the receptor. A typical X-ray tube is comprised of a filament, which also operates as a cathode, and an anode which includes a target. When electrons emitted from the filament strike the anode, X-ray photons are generated. The energy of the resultant X-ray beam is determined by the voltage potential (KVP) between the filament and the anode and the quantity of X-ray photons generated is determined by the rate of electron emission of the filament. Therefore, the filament current, which determines the amount of heating of the filament element, is a key factor in determining the characteristics of the X-ray beam. For each X-ray device manufactured, the characteristics of the primary beam are substantially dependent on the combination of filament current and anode voltage of the tube. An objective of an X-ray control circuitry is to set the proper value of filament current and voltage potential that will "give rise to" the desired energy (KVP) and intensity of the X-ray beam as specified by an operator.

Because diagnostic instrumentation devices subject live patients under conditions which may prove harmful when improperly used, such equipment must meet stringent safety requirements. Typically, the equipment is calibrated at the factory prior to initial use. Then field calibration is required prior to regular operation of the equipment, as well as continuing calibration maintenance to keep the equipment within required tolerances. Prior art calibration techniques involve the process of coupling supplemental calibrating equipment to the X-ray device and fine tuning the x-ray device for meeting calibration tolerances. The most common prior art method for sensing beam current and anode voltage requires the use of dynalyzers. In most instances this method is adequate, as prior art practices have shown, but present difficulties.

Calibration equipment in most instances are supplemental devices which are coupled to the X-ray device for obtaining calibration measurements. That is, the calibration equipment does not provide a true representation of the actual in-circuit parameters when the X-ray device is operating normally, because the calibration equipment is not part of the X-ray device itself.

Further, anode voltage and tube current are not independent parameters. Typically it is difficult to vary one parameter without affecting the other. During calibration it is difficult to keep one parameter constant while attempting to calibrate the equipment for the other parameter. An anode voltage measurement obtained by the use of non-invasive measurement devices still will affect the tube current parameter, such that calibration limitations will restrict the sensitivity of the X-ray device. In the measurement of tube current with external equipment, such as the dynalyzer, the X-ray device is extremely sensitive to current offset problems, due to noise, ground loops and misadjustments. Due to the errors encountered when external devices are connected to the X-ray equipment it is difficult to derive a reliable method to measure tube current externally on prior art X-ray systems. This is especially true in the calibration of a system having low milliampere tube current values. In this instance more error is introduced than is removed during a calibration procedure. Although non-invasive methods may reduce this error somewhat, the potential for calibration induced errors are still present. Also, calibration procedures performed by a calibration technician may require repetitive adjustments of the anode voltage and tube current values to derive at an acceptable tolerance zone.

It is to be appreciated that what is needed is a means to adjust dynamically the X-ray control parameters, KVP and tube current, in response to the internal sensors in a manner that reduces or eliminates the errors that occur due to the use of intrusive test equipment.

It is appreciated that what is needed are permanent sensors which are part of the actual device such that non-invasive calibration measurements can be obtained without altering the operative circuit parameters. Such internal sensors, can then be used for self calibration while the device is functioning.

Also, what is needed is a means to perform a calibration that minimizes the calibration error in an optimum manner. Such a method would utilize data acquired from internal sensors to perform the initial calibration and maintain that calibration over time.

A further concern of modern day X-ray equipment deals with the portability of such equipment. In most instances it is more cost efficient to bring the equipment to the patient instead of bringing the patient to the equipment. The advantage is not only in the cost but concern for the patient in not having to be transported. Therefore, a trend has been to develop a class of mobile X-ray equipment which can be transported to the patient for providing X-ray imaging.

In most instances, these mobile X-ray units are self contained except for the power unit. With the prior art X-ray units a specialized power source is needed to operate the unit. For example, when these units are used in a hospital, a special power source, such as 220 VAC are required to operate the unit. These special power requirements, such as the 220 VAC outlet, severely restrict the mobility of these units because the units must be in proximity to the specialized outlet. Attempts to develop mobile X-ray units which can be plugged into ordinary house current, 110 VAC, could not meet the power requirements necessary for high-intensity beam generation.

It is appreciated that what is required is an X-ray machine which is capable of providing the high voltage and current power source requirement to its X-ray tube such that high precision operation of the device can be achieved, yet having such a device operate from ordinary 110 VAC.

SUMMARY OF THE INVENTION

The present invention provides for a mobile C-arm X-ray imaging machine which is operable from ordinary house current and implements an internal calibration scheme. The X-ray machine is used to obtain film and flouro exposures and a monitor unit is coupled to the machine for viewing image information provided by the machine.

The machine includes a digital processor for providing control signals and analyzing signals obtained during an X-ray exposure. For a given X-ray technique, software provides the initial controls for the anode voltage (KVp) and tube current (mA) of a X-ray tube of the machine. Once the exposure commences, hardware regulation loops provide the controls. Sensing elements within the high voltage section of the machine provide continuous feedback signals to the KVp and mA regulation loops, wherein error signals continuously provide adjustments to maintain regulation of the desired KVp and mA values.

The X-ray machine of the present invention also uses a bank of batteries to provide the necessary power for an exposure. When the exposure is taken, battery power is used and AC input power is used to supplement the batteries. At other times, a battery charger circuit uses the AC input power to charge the batteries. The use of batteries permit the machine to operate using ordinary 110 VAC house current.

BRIEF DESCRIPTION OF THE DRAWINGS

FIG. 1 is a pictorial view of a C-arm X-ray machine of the preferred embodiment.

FIG. 2 is block schematic diagram of the C-arm X-ray machine of FIG. 1.

FIG. 3A is a schematic diagram of a X-ray tube used with the machine of FIG. 1.

FIG. 3B shows waveforms for controlling the filament current of the X-ray tube.

FIG. 4 is a block schematic diagram of a filament current regulator as used in the preferred embodiment.

FIG. 5 is a circuit schematic diagram of the regulator of FIG. 4.

FIG. 6 is a block schematic diagram of an anode voltage regulator as used in the preferred embodiment.

FIG. 7 is a circuit schematic diagram of the regulator of FIG. 6.

FIG. 8 is a circuit schematic diagram of a battery charger of the present invention.

DETAILED DESCRIPTION OF THE INVENTION

A mobile C-arm X-ray imaging system which provides an internal sensor for self-calibration and which can be powered by 110 volt AC is described. In the following description, numerous specific details are set forth such as specific circuits, components, and mechanical descriptions, etc., in order to provide a thorough understanding of the present invention. It will be obvious, however, to one skilled in the art that the present invention may be practiced without these specific details. In other instances, well known circuits and structures have not been shown in detail in order not to unnecessarily obscure the present invention. Moreover, while the present invention is described in connection with a particular power source, the present invention can be used with other equivalent power sources.

Referring to FIG. 1, a mobile C-arm X-ray unit of the preferred embodiment is shown. A principal function of the mobile C-arm X-ray unit 10 is to generate X-rays for diagnostic imaging. Unit 10 is comprised of mainframe 11, C-arm 12, L-arm 13 and control panel 13. The lower portion of mainframe 11 forms a T-shaped structure, wherein conductive castors are utilized to provide mobility of the unit 10. Mainframe 11 includes a power panel 17 for controlling the coupling of power, as well as other devices, to unit 10. Mainframe 11 also includes a vertical lift column 18 which permits the C-arm 12 and L-arm 13 to move vertically in relation to mainframe 11. Vertical lift column 18 terminates in an upper housing 19, wherein horizontal extension arm 20 passes through upper housing 19 and permits arm 20 to move perpendicularly in relation to vertical lift column 18 by the movement of the horizontal extension arm 20 in relation to upper housing 19. With unit 10 of the preferred embodiment, L-arm 13 is capable of pivoting about the horizontal extension arm 20 such that the L-arm 13 can be made to pivot in a 360 degree arc for positioning of the C-arm 12.

The horizontal extension arm 20 is coupled to one end of L-arm 13, while the other end of L-arm 13 is coupled to C-arm 12. C-arm 12 is a "C" shaped structure having an X-ray emitter 23 at one end of the C-arm 12 and an image intensifier 24 and a camera 25 at the other end of C-arm 12. The function of the X-ray tube emitter 23, image intensifier 24 and camera 25 are well known in the prior art in the use of C-arm type X-ray devices utilized for image displays. The C-arm 12 includes a flip-flop lock 28 and flip-flop brake 27 which permit a 180 degree rotation of C-arm 12. The rotation of C-arm 12 permits the X-ray tube assembly to be positioned either above or under in relation to the image intensifier 24 and camera 25. The function of the brake 27 and lock 28 are equivalent to the devices disclosed in U.S. Pat. No. 4,209,706. It is to be noted that X-ray emitter 23 of C-arm 12 is used in conjunction with collimator assembly 29 for providing the collimating function of the X-ray beam from the X-ray emitter 23 and also includes spacer 30 which provides the requisite safety distance that a patient can be brought within the X-ray emitter 23.

It is to be appreciated that although a particular mobile C-arm X-ray unit is shown in FIG. 1, other structures can be readily implemented. The purpose of describing the preferred embodiment as shown in FIG. 1 is to provide a background in which the present invention is utilized. Further, the unit 10 of FIG. 1 is typically coupled to a monitoring unit (not shown) wherein such monitoring unit includes equipment necessary for viewing the video image provided by camera 25. The coupling is accomplished through cables coupled through power panel 17 of unit 10 to the monitoring equipment, such as a video display monitoring cart, which is typically used in conjunction with the C-arm X-ray unit 10.

Referring to FIG. 2, an electrical block diagram of unit 10 of FIG. 1 is shown in a block diagram form. Unit 10 is a computer operated device wherein the processor for controlling the various functions of unit 10 is labelled as a technique processor 35. The technique processor 35 of the preferred embodiment is a digital processor for executing various operation and application computer programs which are stored within memory 36. Memory 36, which is coupled to the technique processor 35 is a micro floppy disk drive unit and memory 36 includes software which is booted to the technique processor 35 each time unit 10 is started. Technique processor 35 is coupled to the control panel 14 by a RS-232 serial link 37.

Control panel 14 also includes a processor for receiving information from manual switches and dials located on the face of control panel 14 and provides digital information to the technique processor 35. The technique processor 35 is also coupled to the monitoring unit by a RS-232 line 38 for transferring information to the monitoring unit. Upper housing 19 includes a lift motor 40, rotation motor 41, rotation motor relay 42 and relay control 43. Rotation motor 41 is used to rotate L-arm 13 about the horizontal axis formed by the horizontal extension arm 20. Lift motor 40 is used to raise or lower the vertical lift column 18. Rotation motor 41 is coupled to rotation motor relay 42 wherein when the rotation motor relay 42 is activated it will cause rotation motor 41 to rotate. Lift motor 40 is coupled to relay control 43. Rotation motor relay 42 is also coupled to relay control 43. Relay control 43 provides the control of the direction of the movement of lift motor 40 as well as the activation of rotation motor relay 42.

The X-ray emitter 23, collimator 29, image intensifier 24 and camera 25 are included in C-arm 12 of FIG. 1. The X-ray emitter 23 of the preferred embodiment is an X-ray tube which emits X-rays. The other units of FIG. 2 are analog interface board 47, generator controller 48, batteries 49, stator transformer 50, tank drive circuit 51, and high voltage tank 52. The generator controller 48 includes a battery charger circuit 53 which is coupled to the batteries 49. An AC power source is coupled to generator controller 48, as well as to upper housing 19. Generator controller 48 is coupled to tank drive circuit 51 for providing necessary control signals determining the extent of the X-ray beam to be generated.

Tank drive circuit 51 is comprised of a driver to drive the filament current and anode voltage of the X-ray tube 23. Tank drive circuit 51 is coupled to the high voltage tank 52 wherein high voltage tank 52 contains the high voltage transformer and filament transformer necessary to power the X-ray tube 23. High voltage tank 52 is coupled to X-ray tube 23 for that power generation. High voltage tank 52 also includes high voltage rectifier and sensing circuits which are used by the generator controller to control the emission of the X-ray from X-ray tube 23. The analog interface board 47 provides the necessary interface of the various analog signals to the technique processor 35 and converts digital control information from the processor 35 to analog signals. Information between the analog interface board 47 and technique processor 35 is transmitted on computer bus 57. Analog interface board 47 is also coupled to relay control 43 for controlling the relays and, further, analog interface board 47 is coupled to collimator 29 to control the focusing of the collimator 29.

Referring to FIG. 3A, the X-ray tube 23 of the preferred embodiment is a rotating anode device, wherein driving coils 31 cause the anode of the X-ray tube 23 to rotate. Such rotating anode X-ray tubes are well known in the prior art. A filament supply 33 is coupled to heat the filament which comprise the cathode. A high voltage source 34 is coupled to the anode and cathode of tube 23, wherein electrons striking a rotating target 32 generates X-rays. It is to be noted that the filament current supplies electrical heating power to the filament that gives use to the tube current which flows in the X-ray tube. Filament current is typically stated in amperes while tube current is stated in milliamperes. The terms "tube current" and "beam current" are used synonymously and refer to the rate of electron flow from cathode to anode within the X-ray tube.

Again referring to FIG. 2, stator transformer 50 is coupled to relay control 43 for receiving control information and generating the necessary driving voltage to activate the rotation of the anode of the X-ray tube 23. The image intensifier 24 receives the X-ray beam from the collimator 24 and provides the imaging, wherein camera 25 generates the corresponding video which is transmitted to the monitoring unit. Camera 25 is also coupled to the technique processor 35 wherein necessary control signals are provided to camera 25.

The purpose of the collimator is to limit the size of the useable X-ray beam and continuous variable collimation is provided by a dual set of leaf collimators located in the collimator 29 and these leaf collimators are used to reduce the size and shape of the X-ray beam from the X-ray tube 23. The control signals are provided by the analog interface board 47. Collimator rotation and closure of the upper set of leaves are motorized and can be controlled by the front panel 14. The image intensifier 24 converts the fluoroscopic X-rays, incident on its face into a visible light image on its output screen. A separate high voltage power supply is required for this image intensification and is included within the image intensifier 24. The image intensifier includes an image amplifier for converting X-rays into visible light. Again, these imaging techniques are well known in the prior art. Further, various power supplies needed to operate the various blocks of FIG. 2, aside from the X-ray tube supply which is located in the high voltage tank, are also included within unit 10, but are not shown on the drawing.

FILAMENT AND HIGH VOLTAGE REGULATION

In the X-ray tube of FIG. 3A, tube current is controlled by varying the temperature of the X-ray tube filament. At the beginning of an exposure, approximately two seconds just prior to the exposure, the filament is preheated to an approximate temperature for the selected exposure. The high voltage applied to the anode of the X-ray tbe is a second parameter which controls the extent of the exposure. Therefore, the combination of the anode voltage, referenced as KVp, and the tube current, referenced as mA, provide a combination of parameters which control the quality of a given exposure. Varying any one of these two parameters will change the factors determining a given exposure and, therefore, these two parameters are critical factors to be controlled.

Further, what is essential is that the values put in by the operator on the control panel 14 of the device correspond to the actual mA and KVp values for the X-ray tube. It is critical that these tubes be calibrated such that the values requested by the operator correspond to the actual mA and KVp values supplied to the tube. Therefore, calibration of the equipment is essential for proper operation.

Traditionally in the past, X-ray units, especially mobile X-ray units, were calibrated by service technicians in the field, wherein a technician would connect supplemental test equipment to take calibration readings. Such supplemental devices are invasive devices and cause erroneous readings by placing an additional load to the actual operating conditions. That is, the calibration procedure using invasive devices takes into account the connection of the additional equipment and true reading of the performance of the machine is not obtainable. As referenced in the background section, even non-invasive devices still reflect conditions which are not present during actual operating condition of the device. The present invention provides for a computerized control of mA regulation and KVp regulation. This regulation is controlled by reading sensing units which are part of the actual device. Therefore, the sensing units are always present and function to operate with a device and because of their continual presence, the X-ray machine can calibrate itself during actual operation.

Referring to FIGS. 2 and 3B, a filament duty cycle and a filament B+ regulation before and during an exposure is shown. The X-ray tube current mA is controlled by varying the temperature of the X-ray tube filament. Prior to the activation of the X-ray beam the filament is preheated to an approximate temperature for the selected technique (exposure). Typically the preheat time period varies but will fall within a time period of seconds. When the operator has set the controls on the control panel 14 for taking an exposure, filament preheat values are calculated by the program which is stored in memory 36 and operated on by the technique processor 35. As shown in FIG. 3B, the filament temperature is controlled by the pulse width duration (the duty cycle) and filament B+ determines the amplitude of the pulse width. As the X-ray exposure is to commence the filament preheat condition has been achieved due to the control provided by the software and the technique processor 35.

However as the exposure begins, the software turns over the control to the hardware regulation loop within generator controller 48 and dynamically regulates the filament current as necessary to obtain the desired value of mA. That is, all of the pre-exposure calculation is achieved by the application program of the technique processor 35, however, once the exposure begins the software defers the responsibility to the hardware regulator to maintain the desired tube current. Although the hardware can regulate the current by adjusting the B+ voltage and the pulse width of the duty cycle, the hardware of the preferred embodiment provides for error correction and regulation by adjusting the filament B+ voltage only. The filament B+ voltage is initially set to a low value by the technique processor 35, such as 140 volts for film mode and 175 volts for flouro mode, but as the exposure commences the B+ is increased by the hardware regulation loop to produce the desired filament current.

Referring to FIG. 4, a hardware implementation of the filament dynamic regulation loop of the preferred embodiment is shown. Three control signals, filament duty cycle, filament B+ control and mA control are provided by the technique processor 35 and coupled to the circuit of FIG. 4 through the analog interface board 47. The filament duty cycle signal is coupled to the pulse width modulator circuit 64 which is then coupled to the switcher circuit 65. Filament B+ control signal is coupled to error amplifier 67. The mA control signal is coupled to amplifier 66 and is compared with the mA sense sigal after the mA sense signal is detected by the mA detect circuit 60. Error amplifier 67, regulator control circuit 61 and regulator 62 comprise the regulation loop. The output of regulator 62 is fed back to amplifier 67 to provide the feedback for the loop. Switch 63 when activated will couple the output of amplifier 66 as an input to amplifier 67.

During the filament preheat phase, filament duty cycle and filament B+ control signals are provided by the technique processor 35. The filament duty cycle signal provides the input to the pulse width modulator 64 for providing information as to the duty cycle of the pulse from modulator 64. This output is then provided to switcher 65. The filament B+ control signal is coupled to amplifier 67 and injected into the regulation loop comprised of amplifier 67, regulator control 61 and regulator 62. At this time, switch 63 is open such that the mA control signal will have no effect on the regulation loop. The regulation loop only responds to the filament B+ control signal from the processor 35 and regulator 62 provides the filament drive voltage, which is controlled by the filament B+ control signal.

Once the preheat stage has been achieved, then the device begins the exposure by turning on the X-ray. As stated above, prior to the exposure, the technique processor calculates the filament duty cycle and the filament B+ voltage necessary to take this particular exposure. The duty cycle and the B+ voltage are preadjusted and filament preheat occurs for approximately 1 to 5 seconds. By utilizing the software a course adjustment of the X-ray tube has been achieved for adjusting the filament current.

When the X-ray exposure begins, switch 63 closes coupling mA control signal to amplifier 67. As the exposure is taken, this regulation loop provides a fine adjustment of the value during the exposure in order to reduce the error between the actual sensed current and the mA control signal. Although the mA control signal provides a value predetermined by the software, the actual current is sensed by the mA detection circuit 60. The output of the mA detection circuit 60 is differenced with the mA control signal in amplifier 66 to determine if any error exists. When the two values differ, an error voltage is produced by amplifier 66 and is coupled to amplifier 67 through switch 63. The error voltage from amplifier 66 will provide the necessary compensation to adjust the output of amplifier 67, wherein the regulator control circuit 61 and regulator 62 will compensate the filament B+ voltage such that the actual value of the tube current is brought to the desired value. When the filament is operating at the proper current level, the mA sense signal when summed with the mA control signal will provide zero error. Therefore, by dynamically and continuously measuring the mA sense signal and adjusting any differences in the filament current by compensating for the error, the filament B+ voltage of the X-ray tube is adjusted to maintain a desired tube current.

In the preferred embodiment, the X-ray tube current is sensed by a one hundred turn toroidal transformer placed around the anode connector inside the high voltage tank. The anode lead, passing through the toroidal act as the transformer primary. The voltage seen at the anode is DC with high frequency ripple. The voltage ripple seen at the anode provides the means for current sensing by transformer action. The ripple induces an alternating current in the secondary winding of the 100 turn sensing transformer that allows tube current to be measured. A high voltage rectifier in the tank prevents the current in the anode lead from reversing. The transformer can be used to measure the DC current as long as the secondary winding current is prevented from reversing. This is achieved by self clamping the input transimpedance amplifier which is used to provide the input coupling amplifier of the detection circuit 60.

Referring to FIG. 5, it shows a circuit implementation of the mA regulation circuit of FIG. 4 as used in the preferred embodiment. The mA sense signal is coupled as an input to a transimpedance amplifier 70 which is then coupled to amplifier 71. Amplifier 71 operates as a four-pole low-pass filter. The output of the amplifier 71 is coupled to film-flouro scaling amplifier 72. Amplifier 72 provides the necessary scaling for providing the desired values for film mode or the flouro mode. Analog switch 73 is controlled by a mA range signal, wherein this mA range signal selects one of two sets of resistors 74 or 75 which determine the amplification factor of amplifier 72.

The mA control signal is inputted to the differential amplifier 78 and the output of amplifier 78 is coupled, along with the output of amplifier 72, to the input of amplifier 79. Amplifier 79 operates as a mA error amplifier and provides the function of the amplifier 66 of FIG. 4. Switch 80, which is controlled by the "KVp ON" signal, is coupled to amplifier 79 and activates amplifier 79 whenever the KVp is turned on. Switch 80 operates equivalently to switch 63 of FIG. 4. The output of error amplifier 79 is coupled along with the filament B+ control signal as an input to regulator 81. Regulator 81 provides the function of summing amplifier 67, regulator control 61 and regulator 62 of FIG. 4. The output of regulator 81 is coupled to the filament push-pull drivers 84 and 85, as well as a feed back signal, to the input of the regulator 81.

Filament drive A and B signals are coupled to provide power for the primary of transformer 86 and the secondaries of the driver transformer 86 are coupled to the push-pull drivers 84 and 85. The output of the drivers 84 and 85 are coupled to the filaments. The filament drive A and B signals are pulse width modulated signals. That is, the pulse width modulator 64 of FIG. 4 has already provided the pulse width modulation necessary for determining the actual duty cycle of the filament voltage. The output of the transistors 84 and 85 are coupled to the filaments for providing the necessary drive. It is appreciated that variations of the circuit of FIG. 5 are possible to achieve an equivalent function without departing from the spirit and scope of the present invention.

Referring to FIG. 6, a block diagram schematic of a high voltage regulator circuit of the present invention is shown. The KVp regulation loop provides dynamic regulation by varying the duty cycle applied to the high voltage driver circuit. The KVp (anode voltage) regulation is achieved by a closed loop regulation system comprising of a KVp sensing circuit (not shown), peak detector 90, sample and hold circuit 91, error amplifier 92, pulse width modulator 93, switcher 94, and switch 95. A primary KVp sense signal is obtained from a capacitive voltage divider (10,000 to 1 ratio divider) located in the high voltage tank. As was the case in the mA sensing, KVp sensing element is always present within the high voltage tank and continuously monitors the actual high voltage present on the X-ray tube. A second method of KVp measurement is provided by a one-turn tap on each side of the high voltage transformer secondary center tap.

The KVp detection circuit 90 functions to separately detect both positive peaks and negative peaks of the KVp sensing waveform. The outputs of the detection circuit 90 are coupled to the zero order hold circuit 91 wherein this sample and hold circuit 91 samples both peaks and then combines and integrates the results of both peaks. Output of the sample and hold circuit 91 is coupled to the error amplifier 92 and is provided as an input to the pulse width modulator 93.

The KVp control signal which originates from the technique processor 35 and is coupled to the high voltage regulator circuit through the analog interface board 47 is also coupled to the error amplifier 92. However, when the X-ray is not on, switch 95 is open and the KVp control signal is not coupled to error amplifier 92. Only when the X-ray is to be on, is switch 95 closed to permit the error amplifier to generate an error voltage by combining the detected KVp sense signal with the KVp control signal. The output of the error amplifier 92 is coupled as an input to the pulse width modulator 93. The output of the pulse width modulator 93 is coupled to the switcher 94 which provides the high voltage drive signal comprised of drive A and B for generating the actual peak high voltage to the X-ray tube. The frequency control signal which is coupled to the pulse width modulator 93 provides the frequency of the pulses and the error signal from the error amplifier 92 provides the control for the duration (pulse width) of the pulse. That is, the frequency control signal controls the frequency and the error amplifier provides the actual duration of the pulse width signal. Therefore, the function of the high voltage regulator circuit is hardware control of the pulse width of the high voltage. This pulse width determines the actual peak anode voltage of the X-ray tube.

Referring to FIG. 7, a circuit implementation of the block diagram of FIG. 6 as used in the preferred embodiment is shown. The KVp sense signal is coupled as an input to buffer 100 and the positive peaks are then detected by peak detector 101. The KVp sense signal is also coupled to the input of inverter 102 and detected by peak detector 103. The output of the peak detectors 101 and 103 are coupled to the sample and hold circuits 104 and 105, respectively. The output of both of the sample and hold circuits 104 and 105 are combined and filtered by capacitor 107 and amplifier 108. Capacitor 107 and amplifier 108 form a low pass filter for de-glitching the two sample and hold outputs.

The output of the amplifier 108 is fed to the negative input of the error amplifier 111. The KVp control signal is coupled to switch 112 and switch 112 is activated by the X-ray on signal. The KVp control signal is coupled to the positive input of error amplifier 111 through switch 112. Switch 112 is equivalent to switch 95 of FIG. 6, and error amplifier 111 is equivalent to error amplifier 92 of FIG. 6. The two inputs to the error amplifier 111 are combined to provide an error signal as an output from amplifier 111. This signal is then coupled to the input of the pulse width modulator 114 which is then coupled to the PAL logic 115 which provide the necessary drive A and drive B to the high voltage driver circuit.

The tank drive circuit 51 and the high voltage tank 52 of the C-arm X-ray unit 10 as shown in FIG. 2 can be comprised of a variety of prior art circuits which are utilized for driving and generating high voltages. The high voltage tank 52 of the present invention is an oil filled tank which is sealed and the high voltage driver stage is comprised of switching drivers having a switching frequency of 2500 Hz. Due to the sinusoidal response of the circuit, longer pulse widths controlled by the pulse width modulation circuit results in higher current in the tank circuit.

CALIBRATION

Calibration of the regulation loops and internal sensors involves measurement of the transfer functions of the entire system and the development of a mathematical relationship that approximates these functions.

The resultant transfer functions are used to calculate the control parameters that will "give rise to" the desired values of KVP and mA. In the preferred embodiment, a set of sixth order polynomials are calculated that relate ACTUAL results to DESIRED results. It is appreciated that, while sixth order polynomials are used, the order may vary depending upon the complexity of the transfer function to be approximated. For KVP calibration, the polynomial takes the form:

$$KV_P \text{ DESIRED} = A_0 + A_1 KV_P \text{ ACTUAL} +$$
$$A_2 (KV_P \text{ ACTUAL})^2 A_3 + \text{mA ACTUAL} +$$
$$A_4 (\text{mA ACTUAL})^2 + KV_P \text{ ACTUAL} \cdot \text{mA ACTUAL}$$

For mA calibration, the polynomial takes the form:

$$\text{mA DESIRED} = b_0 + b_1 KV_P \text{ ACTUAL} +$$
$$b_2 (KV_P \text{ ACTUAL})^2 + b_3 \text{ mA ACTUAL} +$$
$$b_4 (\text{mA ACTUAL})^2 + KV_P \text{ ACTUAL} \cdot \text{mA ACTUAL}$$

In the above equations, "ACTUAL" refers to the technique factors, KVP or mA, that are measured by the sensing devices. "DESIRED" refers to the settings applied to the regulation loops that give rise to the "ACTUAL" values.

The coefficients of these equations are determined by taking several exposures over a broad range of KVP and mA values. The data collected from these exposures are then submitted to a bivariate least squares algorithm that yields the coefficients.

The coefficients are hereafter referred to as vectors and are used to calculate the control parameters to be applied to the regulation circuits to give rise to the required results. Stated another way, A Vector yields a "pre-distorted" value of DESIRED KVP that will, when applied to the control circuitry, will yield an ACTUAL KVP value equal to the true DESIRED KVP.

In an equivalent manner, the pre-distorted value of DESIRED mA is calculated through B Vector. A simultaneous solution of these equations is necessary for proper operation.

Utilizing the same methodology, a set of vectors is desired that characterizes the internal sensors and the relationships between filament voltage duty cycle and the resultant X-ray tube current under various conditions of applied tube voltage. In summary, these vectors are:

A Vector—Relates ACTUAL KVP to DESIRED KVp

B Vector—Relates ACTUAL mA to DESIRED mA

C Vector—Relates ACTUAL KVP to the internal capacitive KVP sensor

D Vector—Relates ACTUAL mA to the internal mA sensor

E Vector—Relates ACTUAL KVP to the one turn tap used for KVp sensing

H Vector—Relates ACTUAL mA to the filament voltage duty cycle.

The calculation of these vectors is an automatic process handled by the computer during the calibration phase. It is appreciated that the calibration is optimum in the least squares sense and eliminates the need for the calibrating technician to become involved in making judgmental tradeoffs as in traditional calibration methods. The primary calibration is accomplished through computation of A, B and H vectors. The calibration of the internal sensors is represented by C, D and E vectors.

Once the C, D and E vectors are derived, all further calibration accomplished through the application of data provided by the internal sensors and operated upon by these vectors. This allows one to change the X-ray tube or other system components and perform a re-calibration without the use of external monitoring devices.

It is further appreciated that, through the use of C, D and E vectors, a "continuous" calibration is effected by modification of A, B and H vectors.

BATTERY AND CHARGER CIRCUIT

The C-arm X-ray unit 10 of the present invention utilizes a battery to supplement the input power for providing the necessary power pulse to generate the X-ray beam. To provide a high degree of imaging a certain power requirement must be supplied to the X-ray tube. Typically, prior art units which are capable of providing quality images are currently being plugged into 220 VAC outlets. Because of input power requirements necessary to operate the X-ray machines, this requirement limits the mobility of such high power X-ray units by localizing them to locations having 220 VAC outlets.

The present invention compensates for the input power requirement by combining the input power with power from batteries which are located within the mainframe 11. Battery operation permits the present invention to be operated from 110 VAC outlets, such that the X-ray unit of the present invention can be plugged into ordinary 110 VAC outlets. In the prior art, high power units of this sort draw current in excess of 30 amps at 220 VAC and require the use of 220 VAC supplies. The preferred embodiment utilizes the 110 VAC to keep the batteries charged. When the X-ray is being emitted during operation, the power pulses are drawn from the battery and supplemented by the 110 VAC. During the time the X-ray is turned on, the power is supplied by the battery and the 110 VAC supply. Because the battery will be drained with continued use, the 110 VAC will charge the battery during periods that the X-ray is not on. The preferred embodiment utilizes six 30 volt battery packs, although such numbers are a design choice. The batteries are 5 ampere-hour sealed lead-acid gel cells in a 200 volt DC stack. The batteries are recharged from the AC line at a 400 watt-second rate. The end result is that the X-ray unit is capable of the high power exposures while being operated from a 110 VAC/20 ampere line.

Referring to FIG. 8, the battery charger circuit 53 as used in the preferred embodiment is shown. The battery charger 53 is a boost regulator which provides a controlled current and voltage to the batteries 49. When the system is first plugged into the AC power line, the charger begins to apply 211 volts DC to the battery circuit. Under low charger current demand, the boost regulator output to the batteries 49 is constant at about 211 volts DC. When the battery voltage decreases during an X-ray exposure, the battery charger 53 will supply additional current needed for the exposure, within the safe limits set by the protection circuitry. If the charger current reaches its maximum output limit (current-limit condition) during battery charging or during an X-ray exposure, the charger voltage is stepped up from 211 volts DC to 230 volts DC. This improves battery recovery after high current demands.

As shown in FIG. 8, 110 VAC is applied to the diodes of the rectifier bridge 120. The output of the bridge rectifier 120 is coupled to the filter provided by capacitor 121 and inductor 122. The output of the filter is then coupled through diode 123. The output of diode 123 is coupled to the pie-filter network comprised of capacitors 124 and 125 and inductor 126. The pie-filter network is coupled through diode 127 to provide a DC output voltage. This DC output voltage provides the supplementation during the exposure, as well as charging the battery.

Current sensing is achieved by coil 128 such that comparator 130 provides the comparison of the sense current to a reference value. When the battery charger current limits, transistor 131, which provides the charger mode selection, is turned on. The activation of transistor 131 places resistor 132 in parallel to the voltage feedback loop comprised of resistors 133, 184 and 185. However, when the charging current falls below 400-600 milliamperes, transistor 131 turns off and the charging voltage drops back to 211 volts DC. Pulse width modulator 134 is a current mode, modulator with a built in 5.1 volt reference. Modulator 134 controls the duty cycle applied to the base of the transistor 135.

The collector of transistor 135 is coupled to the junction of inductor 122 and diode 123 such that when transistor 135 is turned on, the current to inductor 122 increases. Transistor 135 receives no drive voltage when the rectified line voltage is lower than the battery voltage and diode 123 is back biased wherein there is no current flow. When transistor 135 turns on, one side of inductor 122 is grounded through transistor 135 and resistor 138. There is a gradually increasing current flow through the inductor. When the transistor 135 turns off, the inductor 122 supplies current by fly-back action which results in a voltage forwarding biasing diode 123. The pie filter network of 124, 125 and 126 filter the cycle variations. Transistor current feedback is obtained from the emitter resistor 138 and fed back to one side of the differential current sensed input of PWM circuit 134.

When transistor 135 turns off, the fly-back action of inductor 122 boosts the voltage by an amount determined by the on-time. Diode 123 prevents backward current flow when transistor 135 is turned on and allows current flow to the batteries during the fly-back phase. Resistor network comprised of resistors 133, 184 and 185 coupled to diode 123 provides feedback to the invertig voltage sense input of PWM 134. Resistor 185 is adjusted to produce 211 volts DC output.

Transformer 128 and ideal diode 139 develop a voltage across resistor 140 proportional to the charging current in the transformer 128 primary. Amplifier 141 amplifies this signal and provides a charger current sense signal to one input of comparator 130. This signal is also coupled to the current indicator 144 and the resistor network comprised of resistors 146, 147 and 148 provide a signal to a voltage indicator 149. The voltage indicator 149 is also coupled to an over-voltage shutoff protection circuit 150 which output is coupled to PWM 134 for turning off the high voltage if an over-voltage condition is sensed. Although voltage indicator 149, current indicator 144 and over-voltage protection circuit 150 are utilized with the preferred embodiment, these three circuits 144, 149 and 150 are not critical to the operation of the charger circuit of the present invention. Further, clamping diodes 155-159 are utilized to clamp transistor 135 to PWM circuit 134.

It is to be appreciated that although a particular circuit is shown describing the battery charger portion of the present invention, variations to this specific circuit can be used to provide an equivalent function without departing from the spirit and scope of the invention. A distinct advantage over the prior art resides in the fact that the X-ray unit of the present invention can be connected to an ordinary 110 VAC outlet and provide high grade imaging comparable to the images provided by prior art devices requiring 220 VAC outlet for its input power.

Thus a dynamic calibration circuit to control X-ray tube parameters and a battery scheme to allow 110 VAC operation of a mobile C-arm X-ray machine has been described.

I claim:
1. An apparatus having a X-ray emitter and a receptor for providing an image of a X-ray exposure, comprising: input coupling means for coupling said apparatus to an external power source.
   a high-voltage generation means for generating voltage and current needed to generate X-rays for said X-ray exposure;
   a battery coupled to said high-voltage generation means for providing battery electrical power to generate said voltage and current by said high-voltage generation means;
   a charger coupled to said input coupling means, high-voltage generation means and battery for providing additional electrical power to said high-voltage generation means during periods of said X-ray exposure by converting said external power;
   said charger recharging said battery during periods when said additional electrical power is not required by said high-voltage generation means; and
   wherein a combination of said battery electrical power and said additional power provide for an improved image from said X-ray exposure.
2. The apparatus of claim 1, wherein said external power source is approximately 110 VAC.

3. A mobile x-ray machine for providing an image of a x-ray exposure, said X-ray machine having a X-ray tube for generating X-rays and a receptor for receiving said X-rays and providing said image, comprising:
- input coupling means for coupling said machine to an external power source of approximately 110 VAC;
- a high-voltage generation means for generating voltage and current needed to power said x-ray tube;
- plurality of batteries coupled to said high-voltage generation means for providing primary electrical power to generate said voltage and current by said high-voltage generation means during said exposure;
- a charger circuit coupled to said input coupling means, high-voltage generation means and batteries for providing additional electrical power to said high-voltage generation means during periods of said exposure by converting external power from said external power source;
- said charging circuit recharging said batteries during periods of no exposure; and
- wherein a combination of stored power from said batteries supplemented by said external power provides for a higher-powered exposure than alone from either one of said batteries and external power source.

4. The mobile X-ray machine of claim 3 wherein said charging circuit includes a current sensor to detect current being sources from said external power source such that when said current from said external power source exceeds a predetermined value, said charging circuit boosts voltage provided by said charging circuit.

* * * * *